United States Patent [19]

Maahs et al.

[11] 4,175,095

[45] Nov. 20, 1979

[54] PROCESS FOR THE MANUFACTURE OF PENTACHLOROVINYLACETYL CHLORIDE

[75] Inventors: Günther Maahs; Konrad Rombusch, both of Marl, Fed. Rep. of Germany

[73] Assignee: Chemische Werke Huls, A.G., Marl, Fed. Rep. of Germany

[21] Appl. No.: 966,299

[22] Filed: Dec. 4, 1978

[30] Foreign Application Priority Data

Dec. 8, 1977 [DE] Fed. Rep. of Germany ....... 2754670

[51] Int. Cl.$^2$ .................. C07C 57/02; C07C 51/58
[52] U.S. Cl. ................................................ 260/544 Y
[58] Field of Search ................................... 260/544 Y

[56] References Cited

U.S. PATENT DOCUMENTS 4,093,638  6/1978  Muller .............................. 260/544 Y

OTHER PUBLICATIONS

Chemical Abstracts, vol. 79, col. 146,035(t) (1973).
Liebigs Ann. Chem. 600 (1956) 1.
Agnew. Makromol. Chem. 60/61 (1977) 1.

*Primary Examiner*—Gerald A. Schwartz
*Attorney, Agent, or Firm*—Millen & White

[57] ABSTRACT

Pentachlorovinylacetyl chloride is prepared by chlorinating tetrachlorocyclobutenone with a chlorinating agent such as (a) $Cl_2$, optionally in the presence of additives, e.g., phosphorous pentachloride, antimony pentachloride, or oxides, hydroxides or carbonates of metals such as alkali or alkaline earth metals; or (b) phosphorous pentachloride.

10 Claims, No Drawings

PROCESS FOR THE MANUFACTURE OF PENTACHLOROVINYLACETYL CHLORIDE

BACKGROUND OF THE INVENTION

This invention relates to the preparation of pentachlorovinylacetyl chloride.

The structure of the parent acid of the compound prepared by the process of this invention, and of its derivatives, was uncertain for a long time, due to the lack of unambiguous methods of determination (Liebigs Ann. Chem. 600 (1956) 1). For this reason, the alternative name pentachlorocrotonic acid has also found use in the literature (Angew. Makromol. Chem. 60/61 (1977) 1). Only very recently was it possible to unambiguously decide that the structure was that of pentachlorovinylacetic acid.

Pentachlorovinylacetyl chloride has been manufactured in the past by chlorination of 1-ethoxy-pentachloro-1,3-butadiene (A. Roedig and P. Bernemann, Liebigs Ann. Chem. 600 (1956) 1. The latter starting material is, however, not easily accessible, since its yield, when prepared from hexachloro-1,3-butadiene, is only 25 to 30 percent, based on the latter compound. Consequently, a need has continued to exist for a process which produces pentachlorovinylacetyl chloride in a simple and economical manner and with high yields.

SUMMARY OF THE INVENTION

Accordingly, it is an object of this invention to provide such a process.

Upon further study of the specification and appended claims, further objects and advantages of this invention will become apparent to those skilled in the art.

These objects have been attained by providing a process for preparing pentachlorovinylacetyl chloride in a simple manner by chlorinating tetrachlorocyclobutenone.

DETAILED DISCUSSION

Suitable chlorination agents include both chlorine and chlorine donors such as phosphorus pentachloride. The use of chlorine is preferred. The chlorinating agents are in general employed in amounts of 1 to 10 moles based on Cl$_2$, preferably 2-5 moles, per mole of tetrachlorocyclobutenone used, i.e., generally 34.5 to 345 g of chlorine per 100 g of tetrachlorocyclobutenone. The gaseous chlorinating agents in excess of one mole can be recycled.

Surprisingly, the conversions and yields in the reaction of chlorine with tetrachlorocyclobutenone can be increased by means of additives. Suitable additives include antimony pentachloride and phosphorus pentachloride, but preferred additives include alkaline materials, such as oxides, hydroxides and carbonates of metals such as alkali metals and alkaline earth metals, especially alkali metal carbonates and alkaline earth metal carbonates and very particularly sodium carbonate. With sodium carbonate, the reaction of tetrachlorocyclobutenone with chlorine to give pentachlorovinylacetyl chloride surprisingly takes place virtually quantitatively.

The antimony pentachloride and/or phosphorus pentachloride type additives are employed in amounts of 0.1 to 5 percent by weight, preferably of 0.5 to 3 percent by weight, relative to the amount of tetrachlorocyclobutenone employed. The alkaline material additives are employed in amounts of 5 to 30 percent by weight, preferably 10 to 20 percent by weight on the same basis.

Tetrachlorocyclobutenone, required as a starting material, is obtained with high yields and conversions by a not yet published process from hexachlorocyclobutene and a mixture of sulphuric acid and sulphur trioxide at elevated temperatures, e.g., by reaction of 1 mol hexachlorocyclobutene with approximately 1 mol each of sulphuric acid and sulphur trioxide at a temperature of 80° C. within 5 hours. Hexachlorocyclobutene can be obtained from hexachloro-1,3-butadiene in yields of near 100% of theory (DE-OS No. 26 18 557), corresponding to U.S. Pat. No. 4,115,460), for example by rectifying commercial hexachlorobutadiene at a pressure of from 2 to 100 mm Hg with a reflux ratio of from 300:1 to 600:1, subjecting hexachlorobutadiene remaining in the bottoms to a heat treatment at from 150° to 200° C. and then returning it to the rectifying column together with fresh commercial hexachlorobutadiene while withdrawing the product rich in hexachlorocyclobutene over the top. A suitable starting material is not only pure tetrachlorocyclobutenone but also crude tetrachlorocyclobutenone which may, for example, contain hexachlorobutadiene and hexachlorocyclobutene originating from its process of manufacture.

In accordance with this invention, the chlorination of tetrachlorocyclobutenone is preferably carried out at elevated temperatures. However, the reaction temperature is not critical.

The reaction of tetrachlorocyclobutenone with chlorine can in particular be carried out at temperatures of 100° to 180° C., preferably 120°–130° C. In this case, the introduction of chlorine advantageously should be started just prior to the commencement of heating in order to avoid discoloration. The reaction with chlorine donors can in particular be carried out at temperatures of 100° to 110° C.

The pressure used in the chlorination of this invention is not critical. Suitable pressures include atmospheric pressure, and super-atmospheric pressures such as 0.5–5.0 atm.

Suitable reaction times at the above-mentioned temperatures are 1–6 hours, after which times the reaction is generally complete.

For gaseous chlorinating agents, it is preferred that the gas be continuously added to the liquid tetrachlorocyclobutenone and the optional additives in conducting the reaction. However, in all cases, all of the chlorinating agents can be admixed with the tetrachlorocyclobutenone and the optional additives at the beginning of the reaction, e.g., in a bomb, and the reaction conducted as described herein.

It is also preferred that the additives employed be anhydrous.

The crude product obtained after the reaction contains, in addition to pentachlorovinylacetyl chloride, inter alia, unconverted tetrachlorocyclobutenone, excess chlorinating agent and the additives. Excess chlorine dissolved in the reaction product can be removed by degassing. Excess chlorinating agent such as phosphorous pentachloride and additives such as the alkaline substances can be removed, for example, by filtration, the residual amount of reaction solution being recovered from the filter cake by extraction, for example, with hexane, or by introduction into a dilute acid, for example, 5 percent strength sulphuric acid. It is also possible to introduce the entire reaction mixture into the dilute acid. The pure pentachlorovinylacetyl chloride is subsequently obtained from the crude product by rectification. However, it is not necessary to isolate the pure product in every case, since the crude product can also be used, or processed further.

Pentachlorovinylacetyl chloride and the esters prepared therefrom (e.g., alkyl-, halogenated-alkyl-, cycloalkyl-, aryl-, aralkyl-esters) may be used, for example, as activators in the manufacture of high-molecular weight copolymers of ethylene with another α-olefin, with or without a poly-unsaturated olefin, using organo-metallic mixed catalysts (e.g., DE-PS No. 15 95 442).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

240 g of 84.4 percent pure tetrachlorocyclobutenone and 48 g of anhydrous sodium carbonate are introduced into a flask. Chlorine gas (35 g/hr) is introduced, with slow stirring, and the mixture is heated to 120° C. for 6 hours while continuing the introduction of chlorine (a total of 220 g of chlorine being introduced over a period of 6¼ hours, of which ¼ hour is heating-up time). After degassing to remove the chlorine dissolved in the reaction product, and after removing the solid, 301.9 g of a crude product are obtained, from which 10.9 g of tetrachlorocyclobutenone (boiling point 180° C.) and 240.3 g of pentachlorovinylacetyl chloride (boiling point 242° C.) are obtained by rectification. The yield of pentachlorovinylacetyl chloride is 90.1% of theory, relative to the amount of material converted, the conversion being 95.0% of theory.

EXAMPLE 2

19 g/hr of chlorine gas are introduced into a mixture of 65 g of 85.9 percent pure tetrachlorocyclobutenone and 9.75 g of anhydrous sodium carbonate in a cylinder, by passing the gas through a frit at the bottom of the vessel. The mixture is heated to 120° C. while maintaining the flow of the stream of chlorine (total introduction time—6¼ hours, with a heating-up time of ¼ hour:total amount of chlorine 119 g). After removing the dissolved chlorine and the solid, in accordance with the description in Example 1, 82.0 g of a product which still contains 3.2 g of unconverted tetrachlorocyclobutenone and 66.7 g of pentachlorovinylacetyl chloride are obtained, i.e., a yield of 94.3% of theory, relative to the amount of material converted, the conversion also being 94.3% of theory.

EXAMPLE 3

17.5 g/hr of chlorine gas are introduced into a mixture of 50 g of 84 percent pure tetrachlorocyclobutenone and 2.5 g of anhydrous sodium carbonate in a cylinder and the mixture is heated for 6 hours to 120° C. while maintaining the flow of the stream of chlorine (total introduction time 6¼ hours, total amount of chlorine 109 g). After removing the dissolved chlorine and the solid, 61.4 g of a product which still contains 2.5 g of unconverted tetrachlorocyclobutenone and 46.8 g of pentachlorovinylacetyl chloride are obtained, i.e., a yield of 88.2% of theory, relative to the amount of material converted, with a conversion of 94.0% of theory.

EXAMPLE 4

17.5 g/hr of chlorine gas are introduced into a mixture of 50 g of 99 percent pure tetrachlorocyclobutenone and 5 g of anhydrous sodium carbonate in a flask. The mixture is heated for 3 hours to 130° C. (total chlorine introduction time—3¼ hours, with a heating-up time of ¼ hour:total amount of chlorine—57 g). After removing the dissolved chlorine and the solid, the crude product (66.6 g) contains 1.1 g of unconverted tetrachlorocyclobutenone and 61.0 g of pentachlorovinylacetyl chloride, i.e., a yield of 90.9% of theory, relative to the amount of material converted, with a conversion of 98.0% of theory.

EXAMPLE 5

17.5 g/hr of chlorine gas are introduced into a mixture of 50 g of 84.4 percent pure tetrachlorocyclobutenone and 2.5 g of anhydrous $K_2CO_3$ in a cylinder. The mixture is heated for 6 hours to 120° C. (total chlorine introduction time—6¼ hours:total amount of chlorine 109 g), in the course of which the additive dissolved. After cooling, 2.5 g of a solid containing 2.4 g of KCl precipitate. After the dissolved chlorine and the solid have been removed, the crude product (60.8 g) still contains 0.4 g of unconverted tetrachlorocyclobutenone and 51.0 g of pentachlorovinylacetyl chloride, i.e., a yield of 90.8% of theory, relative to the amount of material converted, with a conversion of 99.0% of theory.

EXAMPLE 6

A cylinder is filled with 50 g (0.24 mol) of 99 percent pure tetrachlorocyclobutenone and 10 g of anhydrous sodium carbonate. 51.3 g (0.72 mol) of chlorine gas are introduced at 120° C. in the course of 3 hours through a frit at the bottom of the vessel, with slow stirring. The chlorine dissolved in the reaction product, and the solid, are subsequently removed as described in Example 1 and 61.2 g of a crude product containing 18.9 g of tetrachlorocyclobutenone and 37.1 g of pentachlorovinylacetyl chloride are obtained. The yield is 89.4% of theory, relative to the amount of material converted, with a conversion of 62.5% of theory.

EXAMPLE 7

A bomb tube is filled with 15.4 g (0.078 mol) of 99 percent pure tetrachlorocyclobutenone and 5.5 g (0.078 mol) of chlorine. After sealing the tube, the mixture is heated to 150° C. for one hour. After cooling, and degassing to remove the chlorine dissolved in the reaction product, 21.0 g of a crude product which contains 7.3 g of as yet unconverted tetrachlorocyclobutenone and 4.5 g of pentachlorovinylacetyl chloride are obtained, i.e., a yield of 42.1% of theory, relative to the amount of material converted, with a conversion of 52.3% of theory.

EXAMPLE 8

A bomb tube is filled with 18.6 g (0.09 mol) of 96 percent pure tetrachlorocyclobutenone, 0.3 g of phosphorous pentachloride and 6.4 g (0.09 mol) of chlorine. After sealing the tube, the mixture is heated to 150° C. for one hour. After removing the chlorine dissolved in the reaction product by degassing, and after filtering off the additive, 23.0 g of a crude product which contains 2.6 g of as yet unconverted tetrachlorocyclobutenone and 9.8 g of pentachlorovinylacetyl chloride are obtained, i.e., a yield of 47.6% of theory, relative to the amount of material converted, with a conversion of 84.7% of theory.

EXAMPLE 9

41.2 g (0.2 mol) of 99 percent pure tetrachlorocyclobutenone and 167 g (0.8 mol) of phosphorous pentachloride are heated to the boil, under reflux, for 4 hours in a round flask. After cooling, 140 g of petroleum ether are added; the unconverted phosphorous pentachloride is filtered off; and the petroleum ether is distilled off. The residue is then distilled under a pressure of 4.5 mbars. 29 g of a crude product having a boiling range of 78° to 80° C. under 4.5 mbars, and consisting predominantly of pentachlorovinylacetyl chloride, are obtained.

EXAMPLE 10

To a 1 l flash containing 500 g (1.87 mol) hexachlorocyclobutene (prepared according to DE-OS 26 18 557) contaminated with 2.5% of hexachloro-1.3-butadiene, 341 g fuming sulphic acid (oleum) with 39.8% of sulphur trioxide (molar ratio hexachloro-1.3-butadiene:sulphuric acid:sulphur trioxide=1:1.1:0.9) were added while stirring and the mixture was heated for 5 hours to 80° C. After cooling the reaction product was slowly filled into a mixture of ice and sodium chloride while stirring vigorously and the organic phase was immediately separated from the aqueous phase. A mixture of 326 g tetrachlorobutenone, 25 g hexachlorobutene and 16 g hexachloro-1.3-butadiene was obtained. The yield of tetrachlorocyclobutenone is 90.5% of theory, with a conversion of 92% of theory.

The preceding examples can be repeated with similar success by substituting the generically or specifically described reactants and/or operating conditions of this inventown for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of preparing pentachlorovinylacetyl chloride which comprises chlorinating tetrachlorocyclobutenone with a chlorinating agent.

2. The method of claim 1, wherein the chlorinating agent is chlorine.

3. The method of claim 1, wherein the chlorinating agent is a chlorine donor.

4. The method of claim 3, wherein the chlorine donor is phosphorous pentachloride.

5. The method of claim 2, wherein the chlorinating reaction is carried out in the presence of an additive of antimony pentachloride or phosphorous pentachloride.

6. The method of claim 2, wherein the chlorinating reaction is carried out in the presence of an additive of an oxide, hydroxide or carbonate of an alkali or alkaline earth metal.

7. The method of claim 6, wherein the additive is an alkali metal carbonate.

8. The method of claim 7, wherein the additive is sodium carbonate.

9. The method of claim 2, wherein the chlorinating is conducted at a temperature of 100°–180° C.

10. The method of claims 3 or 4, wherein the chlorinating is conducted at a temperature of 100°–110° C.

* * * * *